United States Patent [19]
Metzger et al.

[11] 4,444,646
[45] Apr. 24, 1984

[54] MEMBRANE CAP ASSEMBLY FOR OXYGEN MONITORS

[75] Inventors: Louis G. Metzger, Closter, N.J.; Albert H. Brand, Briarcliff Manor, N.Y.

[73] Assignee: Becton, Dickinson and Company, Paramus, N.J.

[21] Appl. No.: 490,052

[22] Filed: Apr. 29, 1983

[51] Int. Cl.³ .............................................. G01N 27/46
[52] U.S. Cl. .................................... 204/415; 204/279
[58] Field of Search ............................... 204/415, 279

[56] References Cited

U.S. PATENT DOCUMENTS

| | | | |
|---|---|---|---|
| 2,913,386 | 11/1959 | Clark | 204/415 |
| 3,211,638 | 10/1965 | Halvorsen | 204/415 |
| 3,445,369 | 5/1969 | Porter et al. | 204/415 |
| 3,518,179 | 6/1970 | Bleak et al. | 204/415 |
| 3,575,836 | 4/1971 | Sternberg | 204/415 |
| 3,666,650 | 5/1972 | Doniguian | 204/415 |
| 4,092,232 | 5/1978 | Zetter | 204/415 |
| 4,265,250 | 5/1981 | Parker | 204/415 |
| 4,359,054 | 11/1982 | Leist et al. | 204/415 |

*Primary Examiner*—T. Tung
*Attorney, Agent, or Firm*—Robert P. Grindle

[57] ABSTRACT

An improved membrane cap assembly is provided for polaragraphic oxygen sensors in which a preassembled cap is provided with a membrane mounted for receiving the electrodes thereagainst when the assembly is mounted on the sensor body in such a way that the secured portions of the membrane may slide or move in the secured state to accommodate or receive the electrodes. This has the effect of preventing destructive tension forces against the fragile membrane. Also, because of this arrangement, a more effective quantity of electrolyte is retained by the membrane adjacent the electrodes. This, in turn, has the effect of increasing the life of the assembly prior to electrolyte depolarization, and reducing the times necessary to dismantle and replace the assembly with a new cap, and a fresh quantity of electrolyte.

6 Claims, 2 Drawing Figures

MEMBRANE CAP ASSEMBLY FOR OXYGEN MONITORS

BACKGROUND AND STATEMENT OF THE INVENTION

This invention relates generally to an improvement in the recharging of membrane type polaragraphic oxygen sensors. Specifically, this invention is an improvement over the cap assembly described and claimed in U.S. Pat. No. 3,666,650, issued May 30, 1972, which is incorporated by reference in its entirety herein. Other patents describing earlier devices related to the invention herein include U.S. Pat. Nos. 2,913,386; 3,518,179; 3,445,369; and 3,211,638.

As discussed in U.S. Pat. No. 3,666,650, the "life" of the membrane cap assembly of oxygen monitors of the type disclosed therein depends upon the life of the quantity of electrolyte retained in the cap assembly. That is, when the electrolyte is depolarized, it is necessary to remove the cap assembly, to clean the electrodes, to incorporate a new cap assembly with a new membrane and a fresh quantity of electrolyte. This is a tedious procedure, at best. Therefore, it is desirable to reduce to as few times as possible the necessity of removing the cap assembly and going through the replacement and cleaning procedure. It follows, therefore, that the nature and quantity and handling of the electrolyte, upon installation, is most important so that the electrolyte is depolarized less frequently.

In U.S. Pat. No. 3,666,650 referred to above, a preassembled cap assembly is provided wherein the membrane is a disc with the outer circumferential edges thereof secured between the cap body and a retainer ring. Thus, when the cap body is assembled onto the electrode body by cooperating threads between the two bodies, the extended electrodes have the effect of stretching the mounted membrane to accommodate the inserted electrodes. This stretching procedure has the effect of reducing the quantity of electrolyte between the membrane and the inserting electrode surfaces. Thus, the electrolyte is partially squeezed, as discussed in that patent out of the area defined by the membrane on one hand and the electrodes on the other hand. This, in turn, reduces the life of the cap assembly. While such an assembly is a vast improvement over the assemblies utilizing many parts developed previous to the assembly of U.S. Pat. No. 3,666,650, the life of the assembly between changing and cleaning operations is not as long as desired.

With this invention by contrast, an improved membrane cap assembly is provided in which the membrane disc is secured between the cap body and a retainer in such a manner that the outer circumferential portion of the disc is slidable in its secured state to accommodate and receive the electrodes upon mounting the cap assembly to the sensor body so that the membrane is not stretched. There is less force applied to the electrolyte positioned between the membrane and the inserted electrodes, and the quantity of electrolyte retained is substantially greater. This, in turn, has the effect of increasing the life of the assembly and reducing the number of times that the assembly must be changed and cleaned.

This is achieved by utilizing, as discussed above, a retainer which is press-fit into a counterbore in the end of the cap assembly opposite the bore for receiving the electrode body. The retainer is configured to have an annular portion which is spaced from the cooperating annular surface of the cap body so as to provide an annular space for receiving and retaining the outer circumferential portion of the membrane disc. This, has the effect, of allowing the outer circumferential portion of the membrane disc to slide in its retained area to the extent necessary for accommodating the electrode body when it is inserted into the cap assembly body. Thus, there is no substantial pressure applied to the membrane and the electrolyte retained between the electrode body and the membrane. This allows for a larger portion of the electrolyte to be retained between the electrode tip engaging the membrane and the membrane itself.

Other objects and advantages of this invention will be apparent from the following description, the accompanying drawings and the appended claims.

DETAILED DESCRIPTION OF THE INVENTION

Figure 1:
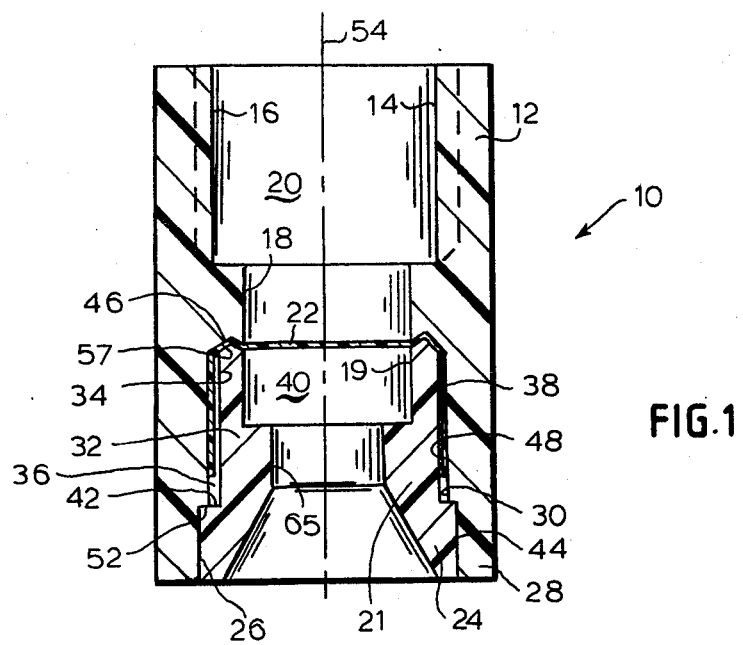
FIG. 1 is a vertical sectional view of a membrane cap assembly for oxygen monitors illustrating the invention prior to mounting of the cap assembly onto the electrode assembly.

Referring to the drawings in which like reference characters refer to like parts throughout the several views thereof FIG. 1 shows the cap assembly of the invention designated generally 10. The assembly 10 includes a generally cylindrical cap body 12 with an axis 54, and having a coaxial bore 14 positioned at one end thereof. The bore 14 includes threads 16 for cooperating with threads (not shown) on an electrode body for a screw fit engagement thereon. The electrode body, as will be understood, is configured substantially as described in the above referred to U.S. Pat. No. 3,666,650 and includes the usual connections to the sensor body 10 as described therein. Cap assembly body 12 includes a secondary bore 18 for receiving the electrode body therein and for defining a space for accommodating the electrode body 50 (FIG. 2) and the bore 14 defines a cylindrical cavity 20 for receiving the electrode assembly connection as described in the above referred to U.S. Patent.

Body 12 includes a counterbore 26 and a secondary counterbore 48 of a lesser diameter than counterbore 26. Counterbore 26 and secondary counterbore 48 are arranged to define a cavity for receiving the membrane retainer body 21 therein. Membrane retainer body 21 includes a lower annular portion 24, the outer surface 44 of which is received in counterbore 26 in a press-fit engagement. As will be understood, these two opposed surfaces may include screw threads for retaining membrane retainer body 21 therein.

Retainer body 21 includes a separate annular portion 32 (FIG. 1) of lesser diameter which defines an annular outer surface 34 which, upon assembly of the arrangement herein opposes the secondary counterbore 48 in cap body 12. These two opposed surfaces are spaced from each other upon assembly to define an annular space 36. This space 36 serves to receive the outer circumferential portion 38 of the membrane disc 22. The point where larger diameter portion 44 meets smaller diameter portion 34 defines an abutment 42 which cooperates with opposed abutment 52 between counterbore 26 and secondary counterbore 48 to limit the insertion of retainer body 21 into cap body 12.

That is, prior to the retainer body 21 being inserted into the cap body 12, the disc 22 is folded over the upper annular portion of retainer body 21, as shown in FIG. 1. Subsequently, retainer body 21 is inserted to provide the pressfit engagement between surfaces 26 and 44. Upon this insertion, the arrangement is as shown in FIG. 1 with the central portion of disc 22 arranged substantially horizontally across chamber 40, as shown in FIG. 1. In this connection, the upper annular edge 57 of retainer body 21 is spaced from the opposed surface 59 of the body 12 to a lesser extent than the opposed surfaces defining annular space 36, to form a gap 46. This gap 46 allows for a sliding movement of membrane 22 therein, but not to an extent where the outer circumferential edges of disc 22 will slide readily out of engagement between retainer body 21 and body 12.

In this connection, the dimensions of annular space 36 are within the range of between about 0.020 inches and 0.030 inches, while the dimension of gap 46 is within the range of between about 0.010 inches and 0.016 inches. Membrane 22 has a thickness preferably within the range of between about 0.001 and 0.003 inches. It may, however, be within the range of between about 0.0005 and 0.006 inches. Preferably, the membrane will be comprised of sintered polytetrafluoroethylene, or equivalent porous material. Other materials which may be used, for example, include sintered polypropylene or polyethylene.

Figure 2:
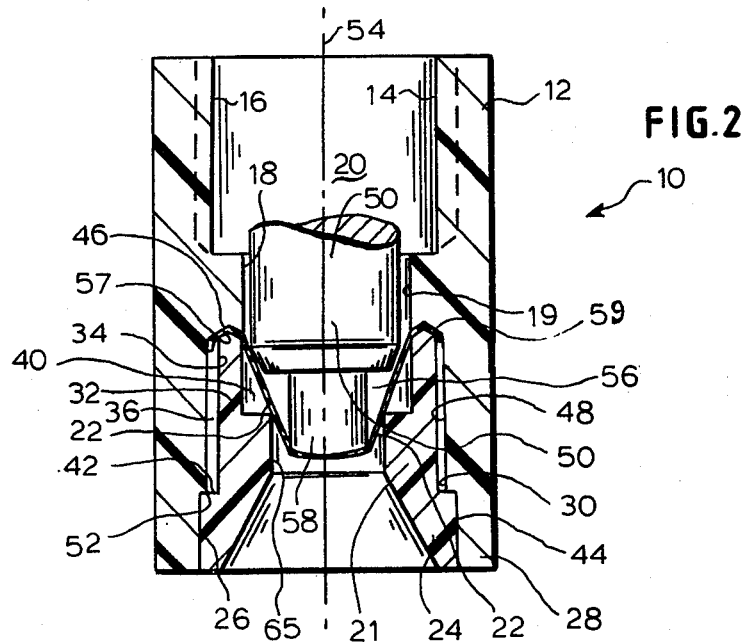
FIG. 2 is a vertical sectional view of the assembly of FIG. 1 mounted or installed on the electrode body assembly shown partially broken away for clarity.

Referring now to FIG. 2, the electrode body 50 is shown inserted into cavity 40 defined by the cooperating annular bores 18 and 19 of cap assembly body 12 and retainer body 21. As can be seen in FIG. 2, the cathode 58 has engaged the membrane 22 so that the outer annular portion 38 thereof has slid out of annular space 36, and so that the most outer annular portion thereof is retained in gap 46. Prior to this assembly and insertion of electrode body 50 into the space 40, an electrolyte was placed in the area defined by membrane 22 and annular bore 18, as shown in FIG. 1. Thus, upon the insertion of the electrode body 50, the membrane "gives" to the extent necessary for receiving the cathode 58 and the remainder of the electrode body 50 in the space 40 to the extent where cathode 58 extends into the bore 65 in retainer body 21, as shown in FIG. 2. This "give" of the membrane has the effect of allowing a greater quantity of electrolyte to be retained in the space 56 defined by the membrane 22 and the electrode body 50, as shown in FIG. 2. A lesser quantity is forced out of the area or space 40 defined by the cooperating bores 18 and 19. This, in turn, allows for a longer life prior to depolarization of the electrolyte confined in the assembled position of the cap assembly of the invention.

As representative of a material which may be utilized for the membrane cap assembly body 12 and retainer body 21, any synthetic resin which is non-reactive to the electrolyte to be used may be selected. Preferably, the resin will be selected to be easily machined and/or molded into the form desired for the parts herein. A representative material is acrylonitrile-butadiene-styrene terpolymer. Other representative materials include polypropylene and polyethylene.

While the methods and forms of apparatus herein described constitute preferred embodiments of the invention, it is to be understood that the invention is not limited to these precise methods and forms of apparatus, and changes may be made therein without departing from the scope of the invention which is defined in the appended claims. For example, counterbore 26 in assembly body 12 may extend without a separate secondary counterbore 48 so as to have retainer body 21 press fit throughout the vertical extent thereof in counterbore 26 of the body. With this arrangement, the membrane 22 will be retained in an elongated extended horizontal gap similar but longer than gap 46 for slide fit engagement and retention therein between the upper annular edge 57 of retainer body 21 and the opposed horizontal surface of cap body 12. While this arrangement is satisfactory for most applications, it does not allow as much of the overall diameter of the membrane disc 22 to be initially engaged in the pre-assembled cap prior to mounting on the electrode assembly.

What is claimed is:

1. Membrane cap assembly apparatus for oxygen monitors, comprising
   (a) a cap assembly body;
   (b) an electrode body receiving bore positioned in one end of said assembly body;
   (c) cooperating attaching means in said bore for attachment to an electrode body; the improvement characterized by
   (d) a counterbore in said assembly body at the end thereof opposite said bore;
   (e) a secondary counterbore in said assembly bore extending from said counterbore;
   (f) the diameter of said secondary counterbore being less than said counterbore;
   (g) an annular retainer inserted into said counterbore and said secondary counterbore;
   (h) cooperating means on the opposed surfaces of said counterbore and said annular retainer for maintaining said retainer in said counterbore;
   (i) the opposed surfaces of said secondary counterbore and said annular retainer being spaced from each other to define an annular membrane retaining space;
   (j) a flat membrane extending across said annular retainer at the end thereof adjacent said secondary counterbore;
   (k) the outer edges of said membrane retained in said annular membrane retaining space;
   (l) the upper annular edge of said annular retainer being spaced from the opposed surfaces of said cap assembly bore to form an annular membrane receiving gap; and
   (m) the width of said gap being less than the width of said membrane receiving space.

2. The apparatus of claim 1, further characterized by
   (a) the width of said annular space being within the range of between about 0.020 inches and 0.030 inches.

3. The apparatus of claim 1, further characterized by
   (a) the width of said gap being within the range of between about 0.010 inches and 0.016 inches.

4. The apparatus of claim 1, further characterized by
   (a) said cooperating means are opposed press-fit engaging surfaces.

5. The apparatus of claim 1, further characterized by
   (a) said annular retainer including a larger diameter portion and a smaller diameter portion;
   (b) the outer surfaces of said larger diameter portion defining said cooperating maintaining means; and
   (c) said smaller diameter portion defining said annular membrane retaining space.

6. The apparatus of claim 5, further characterized by (a) the difference in diameter between said counterbore and said secondary counterbore and the difference between the said cooperating larger and smaller diameter portions of said annular retaining defining opposed abutment means; and
(b) said opposed abutment means defining the extent of insertion of said retainer into said counterbore and said secondary counterbore to define the width of said gap.

* * * * *